United States Patent [19]
Wahl

[11] Patent Number: 5,948,892
[45] Date of Patent: Sep. 7, 1999

[54] ANALOGS OF MACROPHAGE STIMULATING PROTEIN

[75] Inventor: Robert C. Wahl, Thousand Oaks, Calif.

[73] Assignee: Amgen Inc., Thousand Oaks, Calif.

[21] Appl. No.: 08/766,982

[22] Filed: Dec. 16, 1996

[51] Int. Cl.⁶ .......................... A61K 35/16; A61K 38/19
[52] U.S. Cl. .................. 530/380; 514/2; 514/12
[58] Field of Search ................ 530/380; 514/2, 514/12

[56] References Cited

U.S. PATENT DOCUMENTS

| | | | |
|---|---|---|---|
| 4,179,337 | 12/1979 | Davis et al. ............................ | 435/181 |
| 5,219,991 | 6/1993 | Leonard et al. ........................ | 530/351 |
| 5,315,000 | 5/1994 | Degen .................................... | 536/23.5 |
| 5,527,685 | 6/1996 | Leonard et al. ........................ | 435/7.2 |

FOREIGN PATENT DOCUMENTS

| | | |
|---|---|---|
| 0 750 040 A2 | 12/1996 | European Pat. Off. . |
| WO95/28963 | 11/1995 | WIPO . |
| WO96/14082 | 5/1996 | WIPO . |

OTHER PUBLICATIONS

Freizner Degen, SJ et al. Biochemistry. 30:9781–9791, Oct. 1991.
Han, S. et al., Biochemistry. 30:9768–9780, Oct. 1991.
Wang, MH et al. J. Biol. Chem. 269(5): 3436–3440, Feb. 4, 1994.
Carson, *Histotechnology: A Self–Instructional Text* American Society of Clinical Pathologist Press pp. 158–160 (1990).
Degen et al. Biochemistry 30, 9781–9791 (1991).
Donate et al., Protein Science 3, 2378–2394 (1994).
Falk et al., Am. J. Physiol. 266, G987–1003 (1994).
Gaboriaud et al., J. Mol. Biol. 259, 995–1010 (1996).
Leonard et al., Exp. Cell Res. 114, 117 (1978).
Leonard et al., Exp. Cell. Res. 102, 434 (1976).
*Methods of Enzymology* v. 185 (Goeddel, D.V. ed.) Academic Press (1990).
*Remington's Pharmaceutical Sciences*, 18th ed. A.R. Gennaro, ed. Mark, Easton, PA (1990).
Ronsin et al. Oncogene 8, 1195–1202 (1993).
Thery et al., Dev. Genetics 17, 90–101 (1995).
Wang et al., J. Biol. Chem. 269, 3436–3440 (1994).
Wang et al., Science 266, 117–119 (1994).
Whitehead et al., (In Vitro Cellular & Developmental Biology, 23, 436–442 (1987).
Yoshimura et al., J. Biol. Chem 268 15461–15468 (1993).
Zhang et al., J. Biol. Chem. 271, 3884–3890 (1996).
U.S. application No. 08/622,720, filed Oct. 20, 1992.

*Primary Examiner*—David Saunders
*Assistant Examiner*—F. Pierre VanderVegt
*Attorney, Agent, or Firm*—Robert B. Winter; Steven M. Odre; Ron K. Levy

[57] ABSTRACT

MSP analogs which have increased heterodimer formation and enhanced biological activity compared recombinant MSP are provided. The analogs are constructed by substituting unpaired cysteine residues which may interfere with interchain disulfide bonding. DNA sequences encoding MSP analogs, vectors and host cells for the expression of MSP analogs, and pharmaceutical compositions are also provided. The analogs may be used to treat conditions treatable by MSP such as gastrointestinal or hematopoietic disorders.

12 Claims, 7 Drawing Sheets

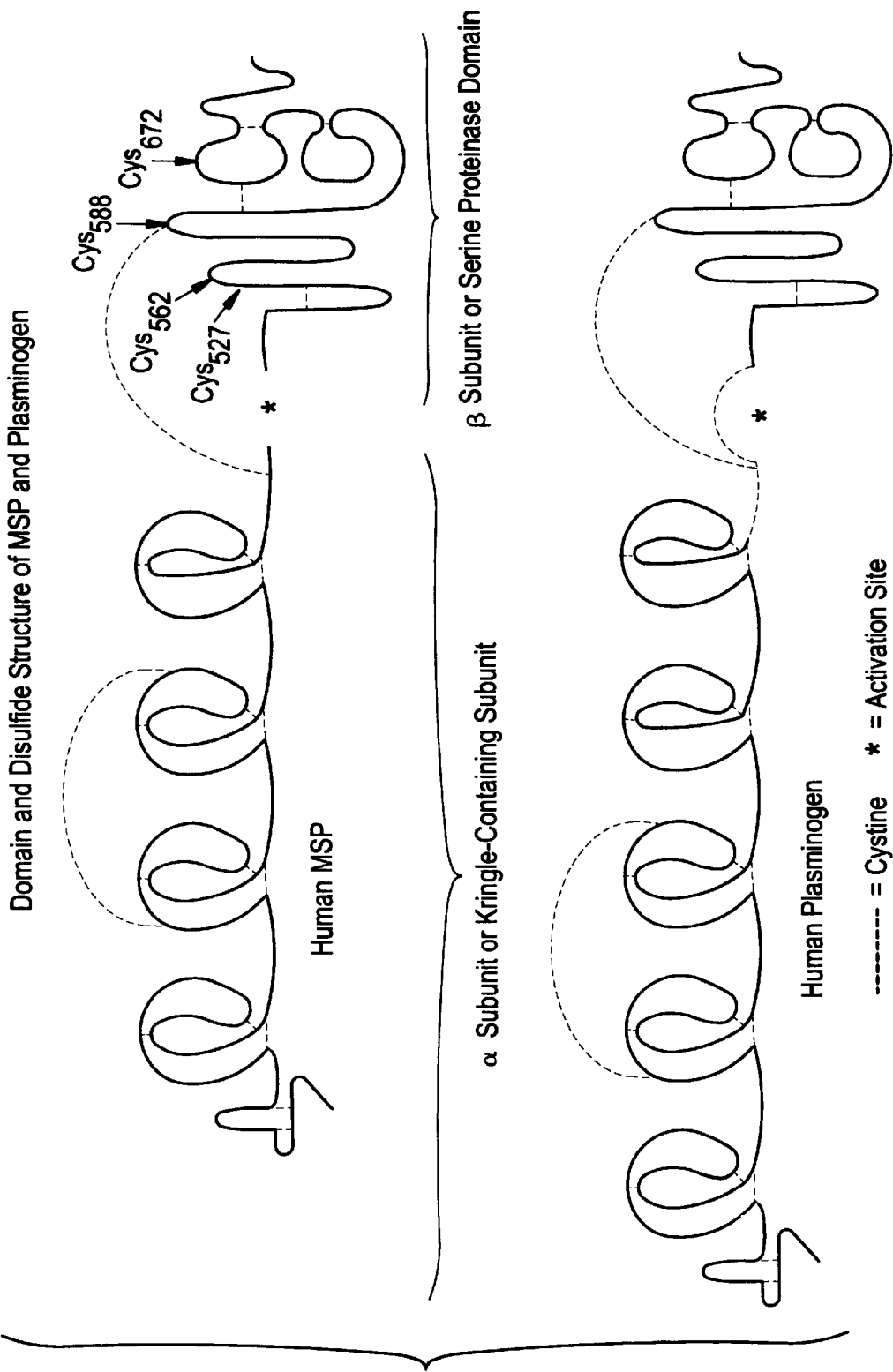

FIG. 2

```
            484
MSP         VVGG...HPG  NSPWTVSLRN  RQGQHFCGGS  LVKEQWILTA  RQCFSSCHMP
Plmn        VVGGCVAHPH  SWPWQVSLRT  RFGMHFCGGT  LISPEWLTA   AHCLEKSPRP
Trypsin     IVGGYNCEEN  SVPYQVSLNS  ..GYHFCGGS  LINEQWVVSA  GHCYK.....
            24                          562                    527
                                                                 66

MSP         LTGYEVWLGT  LFQNPQHGEP  SLQRVPVAKM  VCGPS.....  .GSQLVLLKL
Plmn        .SSYKVILGA  ..HQEVNLEP  HVQEIEVSRL  FLEPT.....  .RKDIALLKL
Trypsin     .SRIQVRLGE  ..HNIEVLEG  NEQFINAAKI  IRHPQYDRKT  LNNDIMLIKL
                                         95

MSP         ERSVTLNQRV  ALICLPPEWY  VVPPGTKCEI  AGWGETKGTG  ND..TVLNVA
Plmn        SSPAVITDKV  IPACLPSPNY  VVADRTECFI  TGWGETQGTF  GA..GLLKEA
Trypsin     SSRAVINARV  STISLPTA..  PPATGTKCLI  SGWGNTASSG  ADYPDELQCL
                          588                                      209
                          127

MSP         LLNVISNQEC  NIKH..RGRV  RESEMCTEGL  LAPVGACEGD  YGGPLACFTH
Plmn        QLPVIENKVC  NRYEFLNGRV  QSTELCAGHL  AGGTDSCQGD  SGGPLVCFEK
Trypsin     DAPVLSQAKC  E..ASYPGKI  TSNMFCVGFL  EGGKDSCQGD  SGGPVVCNGQ
            672

MSP         NCWLEGIII   PNRVCARSRW  PAVFTRVSVF  VDWIHKVMRL  G.
Plmn        DKYILQGVTS  WGLGCARPNK  PGVYVRVSRF  VTWIEGVMRN  N.
Trypsin     ....LQGVVS  WGDGCAQKNK  PGVYTKVYNY  VKWIKNTIAA  NS
```

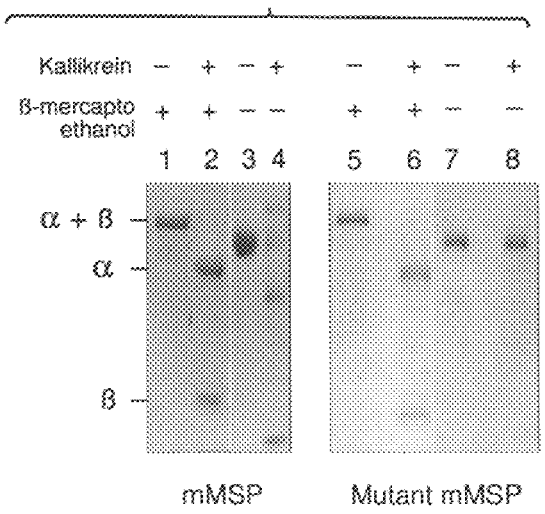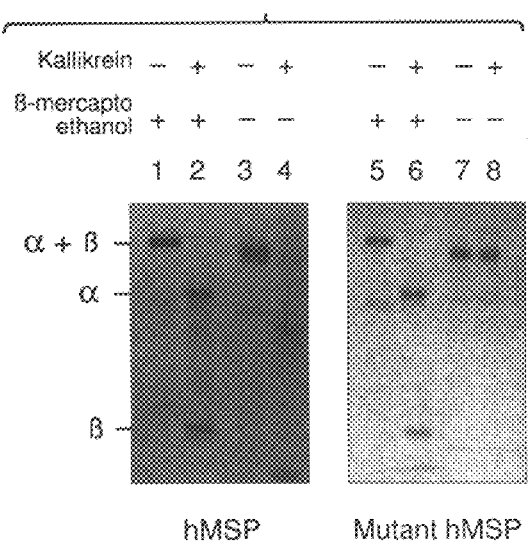

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 716 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Met Gly Trp Leu Pro Leu Leu Leu Leu Val Gln Cys Ser Arg Ala
1               5                   10                  15

Leu Gly Gln Arg Ser Pro Leu Asn Asp Phe Gln Leu Phe Arg Gly Thr
            20                  25                  30

Glu Leu Arg Asn Leu Leu His Thr Ala Val Pro Gly Pro Trp Gln Glu
        35                  40                  45

Asp Val Ala Asp Ala Glu Glu Cys Ala Arg Arg Cys Gly Pro Leu Leu
    50                  55                  60

Asp Cys Arg Ala Phe His Tyr Asn Met Ser Ser His Gly Cys Gln Leu
65                  70                  75                  80

Leu Pro Trp Thr Gln His Ser Leu His Thr Gln Leu Tyr His Ser Ser
            85                  90                  95

Leu Cys His Leu Phe Gln Lys Lys Asp Tyr Val Arg Thr Cys Ile Met
            100                 105                 110

Asp Asn Gly Val Ser Tyr Arg Gly Thr Val Ala Arg Thr Ala Gly Gly
            115                 120                 125

Leu Pro Cys Gln Ala Trp Ser Arg Arg Phe Pro Asn Asp His Lys Tyr
    130                 135                 140

Thr Pro Thr Pro Lys Asn Gly Leu Glu Glu Asn Phe Cys Arg Asn Pro
145                 150                 155                 160

Asp Gly Asp Pro Arg Gly Pro Trp Cys Tyr Thr Thr Asn Arg Ser Val
            165                 170                 175

Arg Phe Gln Ser Cys Gly Ile Lys Thr Cys Arg Glu Ala Val Cys Val
            180                 185                 190

Leu Cys Asn Gly Glu Asp Tyr Arg Gly Val Asp Val Thr Glu Ser
            195                 200                 205

Gly Arg Glu Cys Gln Arg Trp Asp Leu Gln His Pro His Ser His Pro
    210                 215                 220

Phe Gln Pro Glu Lys Phe Leu Asp Lys Asp Leu Lys Asp Asn Tyr Cys
225                 230                 235                 240

Arg Asn Pro Asp Gly Ser Glu Arg Pro Trp Cys Tyr Thr Thr Asp Pro
            245                 250                 255

Asn Val Glu Arg Glu Phe Cys Asp Leu Pro Ser Cys Gly Pro Asn Leu
            260                 265                 270

Pro Pro Thr Val Lys Gly Ser Lys Ser Gln Arg Arg Asn Lys Gly Lys
        275                 280                 285

Ala Leu Asn Cys Phe Arg Gly Lys Gly Glu Asp Tyr Arg Gly Thr Thr
        290                 295                 300

Asn Thr Thr Ser Ala Gly Val Pro Cys Gln Arg Trp Asp Ala Gln Ser
305                 310                 315                 320
```

```
Pro His Gln His Arg Phe Val Pro Glu Lys Tyr Ala Cys Lys Asp Leu
            325                 330                 335

Arg Glu Asn Phe Cys Arg Asn Pro Asp Gly Ser Glu Ala Pro Trp Cys
            340                 345                 350

Phe Thr Ser Arg Pro Gly Leu Arg Met Ala Phe Cys His Gln Ile Pro
            355                 360                 365

Arg Cys Thr Glu Glu Leu Val Pro Glu Gly Cys Tyr His Gly Ser Gly
370                         375                 380

Glu Gln Tyr Arg Gly Ser Val Ser Lys Thr Arg Lys Gly Val Gln Cys
385                 390                 395                 400

Gln His Trp Ser Ser Glu Thr Pro His Lys Pro Gln Phe Thr Pro Thr
                405                 410                 415

Ser Ala Pro Gln Ala Gly Leu Glu Ala Asn Phe Cys Arg Asn Pro Asp
            420                 425                 430

Gly Asp Ser His Gly Pro Trp Cys Tyr Thr Leu Asp Pro Asp Ile Leu
            435                 440                 445

Phe Asp Tyr Cys Ala Leu Gln Arg Cys Asp Asp Gln Pro Pro Ser
450                 455                 460

Ile Leu Asp Pro Pro Asp Gln Val Val Phe Glu Lys Cys Gly Lys Arg
465                 470                 475                 480

Val Asp Lys Ser Asn Lys Leu Arg Val Val Gly Gly His Pro Gly Asn
            485                 490                 495

Ser Pro Trp Thr Val Ser Leu Arg Asn Arg Gln Gly Gln His Phe Cys
                500                 505                 510

Gly Gly Ser Leu Val Lys Glu Gln Trp Val Leu Thr Ala Arg Gln Cys
            515                 520                 525

Ile Trp Ser Cys His Glu Pro Leu Thr Gly Tyr Glu Val Trp Leu Gly
            530                 535                 540

Thr Ile Asn Gln Asn Pro Gln Pro Gly Glu Ala Asn Leu Gln Arg Val
545                 550                 555                 560

Pro Val Ala Lys Ala Val Cys Gly Pro Ala Gly Ser Gln Leu Val Leu
            565                 570                 575

Leu Lys Leu Glu Arg Pro Val Ile Leu Asn His His Val Ala Leu Ile
            580                 585                 590

Cys Leu Pro Pro Glu Gln Tyr Val Val Pro Pro Gly Thr Lys Cys Glu
            595                 600                 605

Ile Ala Gly Trp Gly Glu Ser Ile Gly Thr Ser Asn Asn Thr Val Leu
610                 615                 620

His Val Ala Ser Met Asn Val Ile Ser Asn Gln Glu Cys Asn Thr Lys
625                 630                 635                 640

Tyr Arg Gly His Ile Gln Glu Ser Glu Ile Cys Thr Gln Gly Leu Val
                645                 650                 655

Val Pro Val Gly Ala Cys Glu Gly Asp Tyr Gly Gly Pro Leu Ala Cys
            660                 665                 670

Tyr Thr His Asp Cys Trp Val Leu Gln Gly Leu Ile Ile Pro Asn Arg
            675                 680                 685

Val Cys Ala Arg Pro Arg Trp Pro Ala Ile Phe Thr Arg Val Ser Val
            690                 695                 700

Phe Val Asp Trp Ile Asn Lys Val Met Gln Leu Glu
705                 710                 715
```

(2) INFORMATION FOR SEQ ID NO:2:

(i) SEQUENCE CHARACTERISTICS:
        (A) LENGTH: 711 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:2:

```
Met Gly Trp Leu Pro Leu Leu Leu Leu Thr Gln Cys Leu Gly Val
 1               5                  10                  15

Pro Gly Gln Arg Ser Pro Leu Asn Asp Phe Gln Val Leu Arg Gly Thr
                20                  25                  30

Glu Leu Gln His Leu Leu His Ala Val Val Pro Gly Pro Trp Gln Glu
                35                  40                  45

Asp Val Ala Asp Ala Glu Glu Cys Ala Gly Arg Cys Gly Pro Leu Met
 50                  55                  60

Asp Cys Arg Ala Phe His Tyr Asn Val Ser Ser His Gly Cys Gln Leu
 65                  70                  75                  80

Leu Pro Trp Thr Gln His Ser Pro His Thr Arg Leu Arg Arg Ser Gly
                85                  90                  95

Arg Cys Asp Leu Phe Gln Lys Lys Asp Tyr Val Arg Thr Cys Ile Met
                100                 105                 110

Asn Asn Gly Val Gly Tyr Arg Gly Thr Met Ala Thr Thr Val Gly Gly
                115                 120                 125

Leu Pro Cys Gln Ala Trp Ser His Lys Phe Pro Asn Asp His Lys Tyr
 130                 135                 140

Thr Pro Thr Leu Arg Asn Gly Leu Glu Glu Asn Phe Cys Arg Asn Pro
 145                 150                 155                 160

Asp Gly Asp Pro Gly Gly Pro Trp Cys Tyr Thr Thr Asp Pro Ala Val
                165                 170                 175

Arg Phe Gln Ser Cys Gly Ile Lys Ser Cys Arg Glu Ala Ala Cys Val
                180                 185                 190

Trp Cys Asn Gly Glu Glu Tyr Arg Gly Ala Val Asp Arg Thr Glu Ser
                195                 200                 205

Gly Arg Glu Cys Gln Arg Trp Asp Leu Gln His Pro His Gln His Pro
 210                 215                 220

Phe Glu Pro Gly Lys Phe Leu Asp Gln Gly Leu Asp Asp Asn Tyr Cys
 225                 230                 235                 240

Arg Asn Pro Asp Gly Ser Glu Arg Pro Trp Cys Tyr Thr Thr Asp Pro
                245                 250                 255

Gln Ile Glu Arg Glu Phe Cys Asp Leu Pro Arg Cys Gly Ser Glu Ala
                260                 265                 270

Gln Pro Arg Gln Glu Ala Thr Thr Val Ser Cys Phe Arg Gly Lys Gly
                275                 280                 285

Glu Gly Tyr Arg Gly Thr Ala Asn Thr Thr Thr Ala Gly Val Pro Cys
                290                 295                 300

Gln Arg Trp Asp Ala Gln Ile Pro His Gln His Arg Phe Thr Pro Glu
 305                 310                 315                 320

Lys Tyr Ala Cys Lys Asp Leu Arg Glu Asn Phe Cys Arg Asn Pro Asp
                325                 330                 335

Gly Ser Glu Ala Pro Trp Cys Phe Thr Leu Arg Pro Gly Met Arg Ala
                340                 345                 350

Ala Phe Cys Tyr Gln Ile Arg Arg Cys Thr Asp Asp Val Arg Pro Gln
                355                 360                 365

Asp Cys Tyr His Gly Ala Gly Glu Gln Tyr Arg Gly Thr Val Ser Lys
 370                 375                 380
```

```
Thr Arg Lys Gly Val Gln Cys Gln Arg Trp Ser Ala Glu Thr Pro His
385                 390                 395                 400

Lys Pro Gln Phe Thr Phe Thr Ser Glu Pro His Ala Gln Leu Glu Glu
            405                 410                 415

Asn Phe Cys Arg Asn Pro Asp Gly Asp Ser His Gly Pro Trp Cys Tyr
            420                 425                 430

Thr Met Asp Pro Arg Thr Pro Phe Asp Tyr Cys Ala Leu Arg Arg Cys
        435                 440                 445

Ala Asp Asp Gln Pro Pro Ser Ile Leu Asp Pro Pro Asp Gln Val Gln
450                 455                 460

Phe Glu Lys Cys Gly Lys Arg Val Asp Arg Leu Asp Gln Arg Arg Ser
465                 470                 475                 480

Lys Leu Arg Val Val Gly Gly His Pro Gly Asn Ser Pro Trp Thr Val
                485                 490                 495

Ser Leu Arg Asn Arg Gln Gly Gln His Phe Cys Gly Gly Ser Leu Val
                500                 505                 510

Lys Glu Gln Trp Ile Leu Thr Ala Arg Gln Cys Phe Ser Ser Cys His
            515                 520                 525

Met Pro Leu Thr Gly Tyr Glu Val Trp Leu Gly Thr Leu Phe Gln Asn
530                 535                 540

Pro Gln His Gly Glu Pro Ser Leu Gln Arg Val Pro Val Ala Lys Met
545                 550                 555                 560

Val Cys Gly Pro Ser Gly Ser Gln Leu Val Leu Leu Lys Leu Glu Arg
                565                 570                 575

Ser Val Thr Leu Asn Gln Arg Val Ala Leu Ile Cys Leu Pro Pro Glu
                580                 585                 590

Trp Tyr Val Val Pro Pro Gly Thr Lys Cys Glu Ile Ala Gly Trp Gly
                595                 600                 605

Glu Thr Lys Gly Thr Gly Asn Asp Thr Val Leu Asn Val Ala Phe Leu
        610                 615                 620

Asn Val Ile Ser Asn Gln Glu Cys Asn Ile Lys His Arg Gly Arg Val
625                 630                 635                 640

Arg Glu Ser Glu Met Cys Thr Glu Gly Leu Leu Ala Pro Val Gly Ala
                645                 650                 655

Cys Glu Gly Asp Tyr Gly Gly Pro Leu Ala Cys Phe Thr His Asn Cys
                660                 665                 670

Trp Val Leu Glu Gly Ile Ile Ile Pro Asn Arg Val Cys Ala Arg Ser
                675                 680                 685

Arg Trp Pro Ala Val Phe Thr Arg Val Ser Val Phe Val Asp Trp Ile
            690                 695                 700

His Lys Val Met Arg Leu Gly
705                 710
```

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

ATCCTGAAGG GACAGATTTC                                                              20

(2) INFORMATION FOR SEQ ID NO:4:

```
    (i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:4:

TTTGAGAAGT CTTGACATCT C                                             21

(2) INFORMATION FOR SEQ ID NO:5:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:5:

CCATGACGCC TGGGTCCTAC AG                                            22

(2) INFORMATION FOR SEQ ID NO:6:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:6:

CCATGACGCC TGGGTCCTAC AG                                            22

(2) INFORMATION FOR SEQ ID NO:7:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:7:

CTGGAGAGAC CTGTGATCCT GAACC                                         25

(2) INFORMATION FOR SEQ ID NO:8:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:8:

CACAACGCCT GGGTCCTGGA AG                                            22

(2) INFORMATION FOR SEQ ID NO:9:

(i) SEQUENCE CHARACTERISTICS:
         (A) LENGTH: 23 base pairs
         (B) TYPE: nucleic acid
         (C) STRANDEDNESS: single
```

(D) TOPOLOGY: linear (ii) MOLECULE TYPE: cDNA (xi) SEQUENCE DESCRIPTION: SEQ ID NO:9:

CTGGCAACTA GAAGGCACAG TCG                                              23

(2) INFORMATION FOR SEQ ID NO:10:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:10:

GTGCTTCTCC TCCTGCCATA TGC                                              23

(2) INFORMATION FOR SEQ ID NO:11:

(i) SEQUENCE CHARACTERISTICS:
    (A) LENGTH: 228 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:11:

```
Val Val Gly Gly His Pro Gly Asn Ser Pro Trp Thr Val Ser Leu Arg
1               5                   10                  15

Asn Arg Gln Gly Gln His Phe Cys Gly Gly Ser Leu Val Lys Glu Gln
            20                  25                  30

Trp Ile Leu Thr Ala Arg Gln Cys Phe Ser Ser Cys His Met Pro Leu
        35                  40                  45

Thr Gly Tyr Glu Val Trp Leu Gly Thr Leu Phe Gln Asn Pro Gln His
    50                  55                  60

Gly Glu Pro Ser Leu Gln Arg Val Pro Val Ala Lys Met Val Cys Gly
65                  70                  75                  80

Pro Ser Gly Ser Gln Leu Val Leu Leu Lys Leu Glu Arg Ser Val Thr
                85                  90                  95

Leu Asn Gln Arg Val Ala Leu Ile Cys Leu Pro Pro Glu Trp Tyr Val
            100                 105                 110

Val Pro Pro Gly Thr Lys Cys Glu Ile Ala Gly Trp Gly Glu Thr Lys
        115                 120                 125

Gly Thr Gly Asn Asp Thr Val Leu Asn Val Ala Leu Leu Asn Val Ile
    130                 135                 140

Ser Asn Gln Glu Cys Asn Ile Lys His Arg Gly Arg Val Arg Glu Ser
145                 150                 155                 160

Glu Met Cys Thr Glu Gly Leu Leu Ala Pro Val Gly Ala Cys Glu Gly
                165                 170                 175

Asp Tyr Gly Gly Pro Leu Ala Cys Phe Thr His Asn Cys Trp Val Leu
            180                 185                 190

Glu Gly Ile Ile Ile Pro Asn Arg Val Cys Ala Arg Ser Arg Trp Pro
        195                 200                 205

Ala Val Phe Thr Arg Val Ser Val Phe Val Asp Trp Ile His Lys Val
    210                 215                 220

Met Arg Leu Gly
225
```

(2) INFORMATION FOR SEQ ID NO:12:

(i) SEQUENCE CHARACTERISTICS:
        (A) LENGTH: 230 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Val Val Gly Gly Cys Val Ala His Pro His Ser Trp Pro Trp Gln Val
 1               5                  10                  15
Ser Leu Arg Thr Arg Phe Gly Met His Phe Cys Gly Gly Thr Leu Ile
             20                  25                  30
Ser Pro Glu Trp Val Leu Thr Ala Ala His Cys Leu Glu Lys Ser Pro
         35                  40                  45
Arg Pro Ser Ser Tyr Lys Val Ile Leu Gly Ala His Gln Glu Val Asn
     50                  55                  60
Leu Glu Pro His Val Gln Glu Ile Glu Val Ser Arg Leu Phe Leu Glu
 65                  70                  75                  80
Pro Thr Arg Lys Asp Ile Ala Leu Leu Lys Leu Ser Ser Pro Ala Val
                 85                  90                  95
Ile Thr Asp Lys Val Ile Pro Ala Cys Leu Pro Ser Pro Asn Tyr Val
             100                 105                 110
Val Ala Asp Arg Thr Glu Cys Phe Ile Thr Gly Trp Gly Glu Thr Gln
         115                 120                 125
Gly Thr Phe Gly Ala Gly Leu Leu Lys Glu Ala Gln Leu Pro Val Ile
     130                 135                 140
Glu Asn Lys Val Cys Asn Arg Tyr Glu Phe Leu Asn Gly Arg Val Gln
145                 150                 155                 160
Ser Thr Glu Leu Cys Ala Gly His Leu Ala Gly Gly Thr Asp Ser Cys
                 165                 170                 175
Gln Gly Asp Ser Gly Gly Pro Leu Val Cys Phe Glu Lys Asp Lys Tyr
             180                 185                 190
Ile Leu Gln Gly Val Thr Ser Trp Gly Leu Gly Cys Ala Arg Pro Asn
         195                 200                 205
Lys Pro Gly Val Tyr Val Arg Val Ser Arg Phe Val Thr Trp Ile Glu
     210                 215                 220
Gly Val Met Arg Asn Asn
225                 230
```

(2) INFORMATION FOR SEQ ID NO:13:

(i) SEQUENCE CHARACTERISTICS:
        (A) LENGTH: 224 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

```
Ile Val Gly Gly Tyr Asn Cys Glu Glu Asn Ser Val Pro Tyr Gln Val
 1               5                  10                  15
Ser Leu Asn Ser Gly Tyr His Phe Cys Gly Gly Ser Leu Ile Asn Glu
             20                  25                  30
Gln Trp Val Val Ser Ala Gly His Cys Tyr Lys Ser Arg Ile Gln Val
         35                  40                  45
```

```
Arg Leu Gly Glu His Asn Ile Glu Val Leu Glu Gly Asn Glu Gln Phe
     50                  55                  60

Ile Asn Ala Ala Lys Ile Ile Arg His Pro Gln Tyr Asp Arg Lys Thr
 65              70                  75                      80

Leu Asn Asn Asp Ile Met Leu Ile Lys Leu Ser Ser Arg Ala Val Ile
             85                  90                  95

Asn Ala Arg Val Ser Thr Ile Ser Leu Pro Thr Ala Pro Pro Ala Thr
            100                 105             110

Gly Thr Lys Cys Leu Ile Ser Gly Trp Gly Asn Thr Ala Ser Ser Gly
        115                 120                 125

Ala Asp Tyr Pro Asp Glu Leu Gln Cys Leu Asp Ala Pro Val Leu Ser
        130                 135             140

Gln Ala Lys Cys Glu Ala Ser Tyr Pro Gly Lys Ile Thr Ser Asn Met
145                 150                 155                 160

Phe Cys Val Gly Phe Leu Glu Gly Gly Lys Asp Ser Cys Gln Gly Asp
                165                 170                 175

Ser Gly Gly Pro Val Val Cys Asn Gly Gln Leu Gln Gly Val Val Ser
            180                 185             190

Trp Gly Asp Gly Cys Ala Gln Lys Asn Lys Pro Gly Val Tyr Thr Lys
        195             200                 205

Val Tyr Asn Tyr Val Lys Trp Ile Lys Asn Thr Ile Ala Ala Asn Ser
    210                 215                 220
```

ANALOGS OF MACROPHAGE STIMULATING PROTEIN

FIELD OF THE INVENTION

The invention generally relates to analogs of macrophage stimulating protein, or MSP. More particularly, the invention relates to analogs of MSP which promote multimer formation and have enhanced biological activity.

BACKGROUND OF THE INVENTION

Macrophage Stimulating Protein, or MSP, has been previously identified as an activity present in mammalian blood plasma which makes mouse peritoneal macrophages responsive to chemoattractants such as complement C5a (Leonard et al. Exp. Cell. Res. 102, 434 (1976); Leonard et al. Exp. Cell Res. 114, 117 (1978). MSP was purified from human serum as described in U.S. Pat. No. 5,219,991 and the DNA sequence encoding human MSP was reported in U.S. Pat. No. 5,315,000. MSP is synthesized in a prepro form which is secreted as a single chain polypeptide. The pro form is proteolytically cleaved to form a disulfide-linked heterodimer having an α and β chain of molecular weights 53 kDa and 25 kDa, respectively. The heterodimer is the biologically active form of MSP. It has not been established which protease is responsible for the in vivo activation of MSP, but several proteases, such as human plasma kallikrein are reported to efficiently activate MSP in vitro (Wang et al. J. Biol. Chem. 296, 3436–3440 (1994)).

MSP is a member of a family of proteins having triple disulfide loop structures, or kringle domains (Donate et al. Protein Science 3, 2378–2394 (1994)). Family members include plasminogen and hepatocyte growth factor (HGF). MSP also exhibits sequence homology to both plasminogen and HGF and its proteolytic activation occurs at Arg-Val residues which are also conserved in other family members.

A variety of in vitro biological activities have been reported for MSP. MSP was initially purified based upon stimulation of a chemotactic response of mouse resident peritoneal macrophages (Leonard et al., supra) and was believed to play a role in cell motility. MSP stimulated megakaryocyte maturation and thrombocyte production from isolated bone marrow preparations (PCT Application No. WO96/14082). The in vivo activity of MSP remains to be elucidated.

Recently, it has been reported that MSP is a ligand for RON, a cell membrane protein tyrosine kinase which is a member of the c-met family of protein tyrosine kinases (Wang et al. Science 266, 117–119 (1994); Gaudino et al. EMBO J. 13, 3524–3532 (1994); Ronsin et al. Oncogene 8, 1195–1202 (1993)). The expression of RON in human tissues and cell lines was examined (Gaudino et al., supra) and RON was found to be expressed in colon, skin, lung and bone marrow, and in granulocytes and adherent monocytes. Epithelial cell lines derived from gastric, pancreatic and mammary carcinoma, and hematopoietic cell lines also showed RON expression. MSP induced tyrosine phosphorylation of RON and stimulated DNA synthesis in a mammary carcinoma cell line. These observations suggest that MSP may act on a variety of cell types. MSP promotes colony formation by mouse colon crypts as shown in co-owned and co-pending U.S. Ser. No. 08/622,720, suggesting that MSP may be useful in protecting and regenerating the intestinal epithelium.

In view of the useful biological activities exhibited by MSP, it is desirable to find forms of MSP which have enhanced biological activity. Such forms could provide a more favorable therapeutic regimen in that they can be administered at lower dosages and/or less frequently than MSP.

SUMMARY OF THE INVENTION

The invention provides for analogs of MSP which have increased heterodimer formation and enchanced biological activity compared to recombinant human MSP. The analogs of the present invention are constructed by substituting a cysteine residue with another amino acid such that interchain disulfide bonds will form efficiently and promote MSP heterodimer formation. The resulting MSP analog forms heterodimers of one α (kringle-containing) chain and one β (serine protease) chain to a greater extent than recombinant human MSP. DNA sequences encoding MSP analogs, expression vectors comprising the DNA sequences and modified host cells which express MSP analogs are also provided by the invention. Pharmaceutical compositions of MSP analogs may be used to treat conditions treatable by MSP including gastrointestinal and hematopoietic disorders.

DESCRIPTION OF THE FIGURES

FIG. 1 shows a diagram of the major structural domains of human MSP and human plasminogen, namely the kringle domains and the serine protease domain. Dotted lines show intra and interchain disulfide bridges. Cysteine residues at positions 527, 562 and 672 of MSP represent additional unpaired cysteine which are not conserved in human plasminogen. The asterisk indicates the activation cleavage site which separates the α (kringle) and β (serine protease) domains.

FIG. 2 shows the configuration of conserved Cys residues in the serine protease domains of human MSP, plasminogen, and trypsin. Solid lines indicate the pattern of intrachain disulfide bonds.

FIG. 4 shows 10% PAGE of purified murine (mMSP) or human (hMSP) with Coomassie Blue staining. Some samples were treated with kallikrein (+). Disulfide bonds in some samples were reduced (+β-mercaptoethanol).

DETAILED DESCRIPTION OF THE INVENTION

As used herein, the term "macrophage stimulating protein" or MSP, refers to a protein having kringle domains characteristic of those found in a family that includes plasminogen, prothrombin, and HGF. Macrophage stimulating protein refers to the prepro, pro or mature forms and may be produced recombinantly or by chemical synthesis. MSP may be a single chain precursor or a heterodimer. References to positions in the MSP amino acid sequence are according to the murine and human sequences provided in GenBank accession nos. M74180 and L11924, respectively (also SEQ ID NO:1 and SEQ ID NO:2 for murine and human MSP, respectively).

The term "analog of macrophage stimulating protein" refers to a polypeptide having one or more changes in the amino acid sequence of MSP which enhances heterodimer formation. An MSP heterodimer comprises an α chain of kringle domains linked to a β chain having a serine protease domain.

Expression of recombinant murine MSP in transfected CHO cells was carried out as described in Example 1. After activation in vitro with kallikrein, the resultant material had low specific activity, compared to a sample of active MSP which was purified from bovine serum-containing conditioned media as described in U.S. Pat. No. 5,814,308. Active MSP isolated from human plasma was reported to be a disulfide-linked heterodimer after in vitro kallikrein activation. (Wang et al. supra.) However, recombinant human or mouse MSP was <5% disulfide linked, as judged by SDS-PAGE performed under nonreducing conditions, suggesting that the low activity of recombinant MSP was due to reduced dimer formation.

Figure 3:
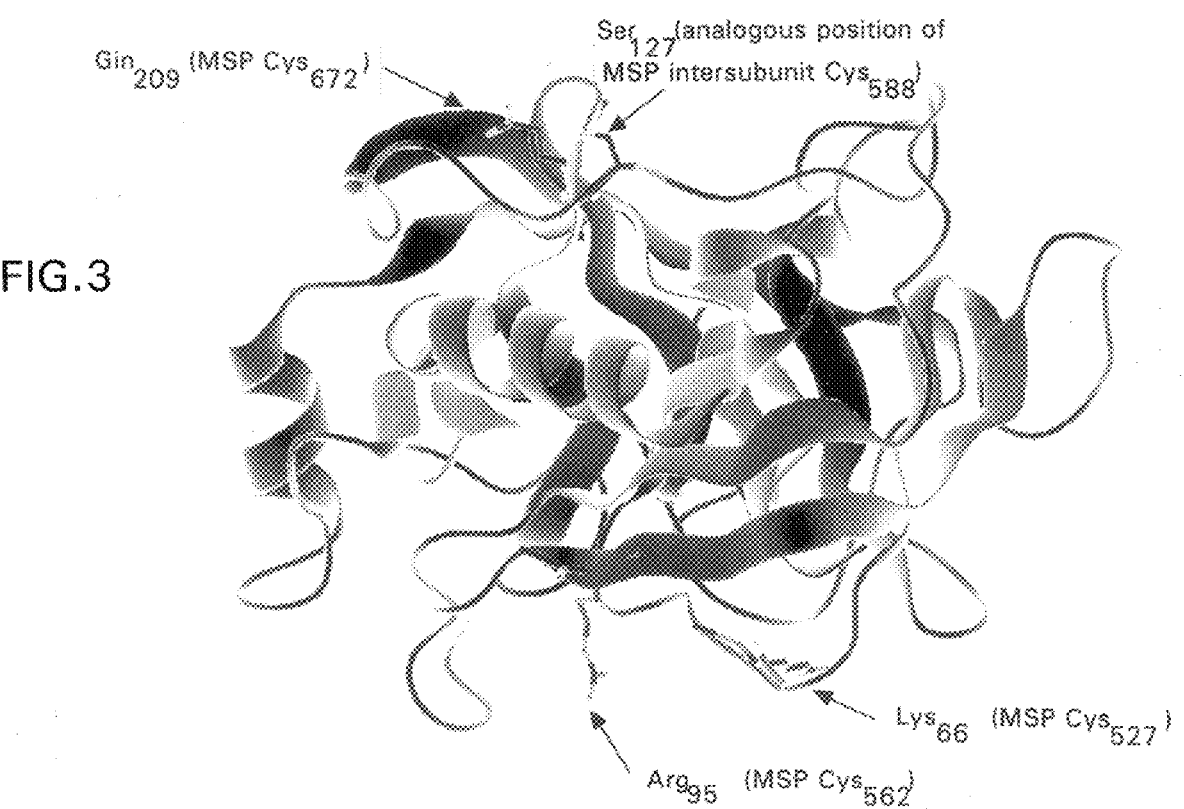
FIG. 3 shows a three-dimensional representation of the serine protease domain of human trypsin. Indicated with labels are the analogous positions of the unpaired and intersubunit cysteine residues of MSP in the three-dimensional structure of human trypsin.

In order to generate highly active recombinant MSP, MSP analogs were constructed that exhibited highly efficient dimer formation. These analogs were constructed with the aid of a model for MSP structure based upon the homology of MSP with plasminogen and other related family members. A comparison of the serine protease (β) domain and disulfide structures of MSP and plasminogen revealed the presence of unpaired cysteine residues in the serine protease domain of MSP, but not in plasminogen. The additional unpaired cysteine residues were also not conserved in HGF. It was postulated that one of the additional unpaired cysteine residues may be interfering with proper intersubunit disulfide bond formation. To determine which residues might be involved, the position of the MSP cysteines was overlaid onto the three-dimensional structure of human trypsin (the structure of diisopropylfluorophosphate-inhibited human trypsin is available from the Brookhaven Protein Database and is reproduced in FIG. 3). Trypsin has only a serine protease domain and lacks kringle regions. As shown in FIG. 3, the use of human trypsin as a framework for visualizing the spatial arrangment of MSP cysteines in the serine protease domain reveals close proximity of Cys 672 with Cys 588, the latter known to be involved in intersubunit disulfide bonding.

Substitution of cysteine residues at postion 672 in human MSP and position 677 in murine MSP is described in Examples 4 and 5. The resulting purified analogs showed enhanced activity in a mouse colon crypt assay compared to recombinant human or murine MSP. In addition, the human analog shows greater stimulation of $^3$H thymidine uptake in RON-expressing cells than human MSP (Example 7).

Accordingly, the invention provides for the first time biologically active MSP analogs. The MSP analogs form heterodimers with greater efficiency than human MSP. In the present embodiment, the MSP analogs have at least one cysteine residue substituted with another amino acid such that interchain disulfide bonds will form efficiently and promote MSP heterodimers. Any unpaired cysteine residue in MSP which interferes with interchain disulfide bonding may be replaced with another amino acid, however it is preferred that a cysteine residue located at positions 677 of murine MSP (SEQ ID NO:1) and position 672 of human MSP (SEQ ID NO:2) be altered.

MSP analogs are constructed and expressed using standard recombinant DNA techniques as described in Examples 4 and 5 of the specification. Unpaired cysteine residues may be replaced by any other amino acid provided the substitution does not perturb the secondary or teritary structure of MSP. It is preferred that substitutions are conservative ones, such as cysteine to serine or alanine.

Expression vectors containing nucleic acid sequences encoding MSP analogs, host cells transformed with said vectors and methods for the production of MSP analogs are also provided by the invention. The vectors comprise cDNA genomic DNA or synthetic DNA encoding MSP analogs. An overview of expression of recombinant proteins is found in *Methods of Enzymology* v. 185 (Goeddel, D. V. ed.) Academic Press (1990).

Host cells for the production of MSP analogs include procaryotic host cells, such as bacterial, yeast, plant, insect and mammalian host cells. Bacterial strains such as *E. coli* HB101 or JM101 are suitable for expression. Preferred mammalian host cells include COS, CHOd-, 293, CV-1, 3T3, baby hamster kidney (BHK) cells and others. Mammalian host cells are preferred when post-translational modifications, such as glycosylation and polypeptide processing, are important for MSP activity. Mammalian expression allows for the production of secreted polypeptides which may be recovered from the growth medium.

Vectors for the expression of MSP analogs contain at a minimum sequences required for vector propagation and for expression of the cloned insert. These sequences include a replication origin, selection marker, promoter, ribosome binding site, enhancer sequences, RNA splice sites and transcription termination site. Vectors suitable for expression in the mammalian, bacterial, plant, yeast, insect host cells are readily available and the nucleic acids of the invention are inserted into the vectors using standard recombinant DNA techniques. Vectors for tissue-specific expression of an MSP analog are also included. Such vectors include promoters which function specifically in liver, kidney or other organs for production in mice, and viral vectors for the expression of an MSP analog in targeted human cells.

Using an appropriate host-vector system, MSP analogs are produced recombinantly by culturing a host cell transformed with an expression vector containing nucleic acid sequences encoding MSP under conditions such that MSP is produced, and isolating the product of expression. MSP is produced in the supernatant of transfected mammalian cells or in inclusion bodies of transformed bacterial host cells. MSP so produced may be purified by procedures known to one skilled in the art as described below. The expression of MSP analogs is described in Example 4 and 5 below. It is anticipated that the specific plasmids and host cells described are for illustrative purpose and that other available plasmids and host cells could also be used to express the polypeptides.

The invention also provides for purified and isolated MSP analogs. The polypeptides of the invention are purified from other polypeptides present in transformed host cells expressing an MSP analog, or are purified from components in cell cultures containing the secreted protein. In one embodiment, the polypeptide is free from association with other human proteins, such as the expression product of a bacterial host cell. The purified protein may be a pro form of an MSP analog, a heterodimer, or isolated α and β chains.

Modifications of MSP analog polypeptides are encompassed by the invention and include post-translational modifications (e.g., N-linked or O-linked carbohydrate chains, processing of N-terminal or C-terminal ends), attachment of chemical moieties to the amino acid backbone, chemical modifications of N-linked or O-linked carbohydrate chains, and addition of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of MSP analogs which may provide additional advantages such as increasing stability and circulating time of the polypeptide, or decreasing immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule, and may include one, two, three or more attached chemical moieties. In a preferred embodiment, the MSP analogs are selectively derivatized at the amino-terminus of the polypeptide.

The invention provides for MSP analog chimeric proteins wherein an analog is fused to a heterologous amino acid sequence. The heterologous sequence may be any sequence which allows the resulting fusion protein to retain the activity of MSP. The heterologous sequences include for example, immunoglobulin fusions, such as Fc fusions, which may aid in purification of the protein. A heterologous sequence which promotes formation of MSP heterodimers is preferred.

A method for the purification of MSP analogs is also included. The purification process may employ one or more standard protein purification steps in an appropriate order to obtain purified protein. The chromatography steps can include ion exchange, gel filtration, hydrophobic interaction, reverse phase, chromatofocusing, and affinity chromatography.

MSP analogs are used advantageously for the treatment of any condition requiring MSP. Examples of such conditions include gastrointestinal disorders and hematopoietic disorders. As the analogs of the present invention have a higher activity compared to human MSP, the analogs may be therapeutically effective with a smaller dosage and/or less frequent administration than human MSP.

The invention provides for the treatment of disorders of the lining of the gastrointestinal tract by administration of a therapeutically effective amount of an MSP analog. The treatment provided herein is particularly useful for disorders involving the intestinal epithelium. The factors of the present invention can modulate the proliferation or differentiation of intestinal epithelium, thereby protecting healthy epithelium from damage and inducing repair and/or regeneration of damaged or depleted epithelium. Administration of an MSP analog may occur prior to, concurrent with, or after the onset of a disorder of the gastrointestinal tract lining for a time and a concentration sufficient to protect, repair and/or regenerate the gut lining.

As used herein, a "therapeutically effective amount" refers to that amount of MSP which provides a therapeutic effect for a given condition and administrative regimen. Said amount may vary from 0.1 μg/kg body weight to 1000 mg/kg body weight and may be more precisely determined by one skilled in the art.

Efforts to aggressively treat cancer have led to the administration of higher doses of chemotherapeutic agents or the use of whole body radiation, but such regimens can lead first to bone marrow toxicity (depletion of red blood cells and white blood cells) followed by gut toxicity (depletion of intestinal epithelium). It is usual that a dose reduction or a cessation of therapy occurs until the toxicity is overcome. A preferred method of treatment is the use of MSP as an adjunct to chemotherapy or radiation therapy, either prior to or concurrent with such therapy. MSP may help maintain or repair epithelial cell linings in the intestinal tract and thereby prevent or reduce the occurrences of reduction or cessation of therapy.

Certain disease states may also lead to damage or depletion of intestinal epithelium and may be treated by administration of MSP. Examples include inflammatory bowel disease, a class of diseases including ulcerative colitis and Crohn's disease, duodenal ulcers or infections. Administration of MSP will help restore normal intestinal mucosa where damage has occurred.

It is understood that MSP may be used alone or in conjunction with other factors for the treatment of intestinal epithelial disorders. In one embodiment, MSP is used in conjunction with a therapeutically effective amount of a factor which promotes epithelial cell growth. Such factors include insulin growth factor-1 (IGF-1), insulin growth factor-2 (IGF-2), epidermal growth factor (EGF), transforming growth factor-a (TGF-a), acidic and basic fibroblast growth factor (FGF), platelet derived growth factor (PDGF), keratinocyte growth factor (KGF), interleukin-6 (IL-6) or interleukin-11 (IL-11).

The invention provides for the treatment of hematopoietic disorders involving a deficiency in megakaryocytes or thrombocytes by administering a therapeutically effective amount of an MSP analog. Such conditions can arise from disease or exposure to myelosuppressive agents. In one embodiment, an MSP analog may be used to treat thrombocytopenia resulting from exposure to radiation or chemotherapy. An MSP analog may be used alone or in conjunction with other hematopoietic factors which stimulate megakaryocyte or thrombocyte levels. Hematopoietic factors to be used in conjunction with MSP include erythropoietin (EPO), granulocyte colony stimulating factor (G-CSF), megakaryocyte growth and differentiation factor (MGDF), granulocyte macrophage colony stimulating factor (GM-CSF), stem cell factor (SCF), interleukin-3 (IL-3) or interleukin-6 (IL-6).

MSP may be administered by a variety of routes including parenteral, oral, nasal or rectal administration. Parenteral administration may occur by intravenous, subcutaneous, intradermal, intramuscular, intraarcticular and intrathecal injection. Oral administration involving adsorption through the gastrointestinal tract uses compressed tablets, capsules, pills, troches, cahcets and pellets. Adminstration by the nasal or oral respiratory route may employ powdered or liquid polypeptide delivered as an aerosol. Nasal delivery includes administration by drops or sprays. Rectal administration may employ suppositories. The route of administration to be chosen will depend upon several variables, including the pharmacokinetic properties of MSP and the nature and severity of the condition being treated.

The invention provides for a pharmaceutical composition comprising a therapeutically effective amount of an MSP analog and a pharmaceutically acceptable diluent, carrier, preservative, emulsifier, and/or solubilizer. Diluents include Tris, acetate or phosphate buffers; solubilizers include Tween, Polysorbate; carriers include human serum albumin; preservatives include thimerosol and benzyl alcohol; and anti-oxidants include ascorbic acid. MSP analogs may also be conjugated with water soluble polymers (e.g, polyethylene glycol) using materials and method available to one skilled in the art in order to improve solubility, serum half-life, stability and bioavailability.

MSP analogs may be present in formulations for use in particular delivery systems. As an example, MSP analogs may be formulated for controlled delivery over a period of time. Such formulations include but are not limited to the following: encapsulation in a water insoluble polymer of hardened gelatin, methyl and ethyl celluloses, polyhydroxymethacrylate, hydroxypropylcellulose, polyvinylacetate and various waxes used alone or in combination; dispersion in an inert polymeric matrix of insoluble plastic, hydrophilic polymers, or fatty compounds; and coating with a water soluble polymer such as a shellac, wax, starch, cellulose acetate phthalate or polyvinylpyrrolidone. MSP analogs may also be formulated for a targeted delivery system by entrapment within phospholipid vesicles. In a preferred embodiment, MSP analogs may be incoporated in a cocoa butter or polyethylene glycol base for inclusion in a suppository for rectal delivery. In another preferred embodiment, MSP analogs may be incorporated into a colon-specific drug release formulation such as that described in PCT Application No. WO95/28963.

A more extensive survey of components commonly found in pharmaceutical compositions and formulations is presented in *Remington's Pharmaceutical Sciences*, 18th ed. A. R. Gennaro, ed. Mack, Easton, Pa. (1990), the relevant portions of which are incorporated by reference.

The following examples are offered to more fully illustrate the invention, but are not construed as limiting the scope thereof.

EXAMPLE 1

Mouse Colon Crypt Colony Formation Assay

An assay for colony formation by isolated mouse colon crypts was previously described in U.S. Pat. No. 5,814,308 hereby incorporated by reference. The assay is performed as follows. Mouse colon crypts were prepared as described in Whitehead et al. (In Vitro Cellular & Developmental Biology, 23, 436–442 (1987)). Mice were sacrificed with lethal dose of $CO_2$, and large intestines were isolated. The large intestine was cut longitudinally, rinsed with PBS containing 0.3 mg/ml L-Glutamine, 100 units/ml penicillin, 100 units/ml streptomycin (Buffer A), and sliced to 0.5 cm pieces. The sliced colon pieces were washed several times with buffer A in a 50 ml conical tube. The clean tissue was washed with the extraction buffer (0.5 mM DTT, 2 mM EDTA in buffer A), and then incubated with 10 ml of fresh extraction buffer for 1 hour. The extraction buffer was then removed, and tissue was washed with Solution A. The crypts were harvested by shaking the tissue in 5 ml of Solution A.

Harvested crypts were plated on collagen type IV coated 6 well plates (Collaborative Biomedical Products, Bedford, Mass.) at a density of 500 crypts per well in 4 ml medium (RPMI 1640, 0.3 mg/ml L-Glutamine, 100 units/ml penicillin, 100 units/ml streptomycin, and 10% fetal bovine serum (FBS; GIBCO-BRL. Gaithersburg, Md.). After 24 hours incubation at 37° C., colonies of attached cells were stained with crystal violet, and counted under microscope. To confirm that the cells in the colonies are derived from crypt epithelium, the colonies were stained with McManus' Periodic Acid-Schiff method and Trichosantes kirilowii as described (Carson, *Histotechnology: A Self-Instructional Text* American Society of Clinical Pathologist Press pp. 158–160 (1990); (Falk et al. Am. J. Physiol. 266, G987–1003 (1994)). The colonies were compared to mouse colon paraffin sections stained with the same methods. The results of crypt cell staining revealed that both methods are specific for epithelial cells in the colon sections and stained positive for the colonies.

EXAMPLE 2

Activity of natural bovine MSP and recombinant MSP

The colony forming activity of natural bovine MSP and recombinant murine MSP was compared in the mouse colon crypt assay described in Example 1. Bovine MSP was isolated from bovine fetal serum as described in U.S. Pat. No. 5,814,308. Recombinant murine MSP was prepared as follows: A 2266 bp fragment was amplified from cDNA made from mouse liver poly(A)+ RNA by using the following oligonucleotide primers:
ATCCTGAAGGGACAGATTTC (SEQ ID NO:3) and
TTTGAGAAGTCTTGACATCTC (SEQ ID NO:4)
The primers were based on the published mouse MSP sequence (Degen et al. Biochemistry 30, 9781–9791 (1991)). Due to the presence of several mutations in the coding region of the PCR product, the cloned fragment was used as a probe to screen a mouse liver cDNA library (Clonetech). A positive clone with 2.2 kb insert was isolated and sequenced. The DNA sequence that was obtained indicated that this clone contains the coding region of mouse MSP except for the first two amino acids. To obtain the full-length cDNA, an adaptor including the optimal context for initiation of translation and the missing nucleotides was synthesized based upon the published sequence, and ligated to the 2.2 kb insert. The cDNA was subcloned into pcDNA3 vector (Invitrogen). The mouse MSP plasmid DNA was tranfected into COS-7 cells with lipofectamine transfection system (GIBCO BRL). Serum-free condition media were harvested two days after transfection. Murine MSP was purified as described in Example 6 below.

The colony forming activity of natural bovine MSP and recombinant murine MSP was assayed at 2 ng/ml and 10 ng/ml and the results shown in Table 1. Recombinant murine MSP stimulated colony formation by murine crypts about 3 to 7-fold lower than natural bovine MSP.

TABLE 1

Comparison of crypt colony forming activity of native bovine MSP and recombinant murine MSP

| Sample | concentration | # of colonies |
|---|---|---|
| no addition | not applicable | 16 |
| fetal bovine serum | 10% | 118 |
| native bovine MSP | 2 ng/ml | 234 |
| native bovine MSP | 10 ng/ml | 336 |
| recombinant murine MSP | 2 ng/ml | 28 |
| recombinant murine MSP | 10 ng/ml | 118 |

EXAMPLE 3

Modelling of MSP Interchain Disulfide Bonding

The domain and disulfide structures of plasminogen and plasminogen-related growth factors are shown in FIG. 1. From the N-terminus, the domain structure of plasminogen may be summarized to contain a secretion signal peptide, an N-terminal "hairpin" domain, 5 kringle domains, and a serine proteinase domain (SPD). The domain structures of MSP and HGF are very similiar to that of plasminogen. The main difference is that MSP and HGF have only four kringles due to the deletion of kringle 5 of plasminogen. The disulfide structure of plasminogen contains intra and interdomain disulfide bonds: The intradomain disulfide bonds may be listed as follows: the hairpin domain contains two disulfides, each kringle contains 3 disulfides and the SPD contains 4 disulfides. There is an interdomain disulfide between the second and third kringle, and two disulfides between the last kringle of the α subunit and the SPD. As shown in FIG. 2 of Thery et al. (Dev. Genetics 17, 90–101 (1995) and in FIG. 1 below, every disulfide that is present in plasminogen is also present in HGF and MSP, with one exception: HGF and MSP have only a single disulfide between the kringle-containing (α) subunit and the serine proteinase domain (β). HGF from chicken, mouse and human contain no extra Cys or disulfides other than those which are homologous to plasminogen. MSP, however contains extra Cys, some of which are conserved in chicken, mouse, and human. Thus, murine MSP has a Cys residue in the signal sequence, and MSP from mouse and human contain an extra Cys in the hairpin domain. MSP from all three species contain 3 extra conserved Cys in the SPD compared to both plasminogen and HGF. Since recombinant HGF of high specific activity is available commercially and recombinant MSP is not, we considered whether the extra conserved Cys residues of MSP were involved with the disufide bonding defect that we observed with our recombinant MSP preparation.

Although high resolution structural information is not available for plasminogen, MSP or HGF, this information is available for other serine proteinases, such as trypsin. Mature trypsin contains only a serine proteinase domain, which is formed by the removal of a 15 residue signal peptide and a 9 residue activation peptide. Since trypsin has very high sequence homology to the serine proteinase domain of MSP (or plasminogen), we used the structure of trypsin as a surrogate for the SPD of MSP. The Brookhaven data file 1trn, which is a structure of diisopropylfluorophosphate-inhibited human trypsin, was used for our modelling (See FIG. 3). Trypsin has ten Cys residues that form five disulfide bonds. Four of the trypsin disulfide bonds have homologs in MSP (and plasminogen). The residue numbering system for human trypsin in the structure file from Brookhaven (1trn) is based upon the conventional chymotrypsinogen relative amino acid numbering (Gaboriaud et al. J. Mol. Biol. 259, 995–1010 (1996)) and differs from the residue numbering system in the human trypsin sequence file from Swiss-Prot (try1_human.swiss). Therefore, the residue numbers from the various database files are correlated in Table 2 for clarification.

TABLE 2

Correlation of residue numbers of human MSF and trypsin from various database files   Cysteines of interest in human MSF are compared to chosen homologous residues of human trypsin.

| Human MSF[a] | Cys527 | Cys562 | Cys588 | Cys672 |
|---|---|---|---|---|
| Human trypsin[b] | Lys66 | Arg95 | Ser127 | Gln209 |
| Human trypsin[c] | Lys60 | Arg90 | Ser122 | Gln204 |

[a]Residue numbers as in Swiss-Prot database file HGF1_human.swiss
[b]Residue numbers as in Swiss-Prot database file tyr1_human.swiss
[c]Residue numbers as in Brookhaven database file 1trn Using the the numbering from the structural file, the following trypsin residues were chosen as homologs of the three "extra" Cys residues in MSP: Cys537=trypsin Lys60, Cys562=trypsin Arg90, Cys672=trypsin Gln209, and the intersubunit Cys588=trypsin Ser122. Lys60 and Arg90 are located on the surface of trypsin on the opposite side of the protein from the Ser122. Gln209 and Ser122 are located on the surface in very close proximity, the distance between the α carbons of these residues is 6.1 A. For comparison, the distances between the α carbons of the disulfide bonded Cys residues of trypsin range from 4.2 to 6.2 A. Thus, the suggested close proximity of Cys672 to Cys588 suggests that intra subunit disulfide formation between these two Cys might interfere with intersubunit disulfide formation by Cys588. It should be noted that Cys672 apparently has no other Cys residue other than Cys588 with which to interact.

EXAMPLE 4

Construction and Expression of Murine MSP Analog

Construction of C677A Mutant of Murine MSP

To mutate the cysteine residue which is suspected of interfering with interchain disulfide bond formation, we employed a two-step PCR process. First, murine MSP plasmid template was amplified with a mutant primer (which incorporated a change from TG to GC at nucleotides 2029 and 2030, resulting in a Cys to Ala mutation) and a downstream primer complementary to vector pCDNA3. Primer sequences are:

Mutant: 5' CCA TGA CGC CTG GGT CCT ACA G 3' (SEQ ID NO:5)
Downstream: 5' CTG GCA ACT AGA AGG CAC AGT CG 3' (SEQ ID NO:6)

Cycling conditions were: 96° C., 30 sec.; 62° C., 30 sec; 72° C., 1 min for 5 cycles, followed by an additional 15 cycles at 96° C., 30 sec; 67° C., 30 sec; 72° C., 1 min. A primary 334 base pair product was purified from an agarose gel.

Next, the primary PCR product (containing the Cys to Ala mutation) was combined with a small amount of the original MSP plasmid and cycled in the absence of oligonucleotide primers for 5 cycles. This allowed the upstream and downstream extension of the mutated PCR product. Primers corresponding to an upstream region (nucleotides 1735–1759) of mMSP and the downstream vector primer (above) were added, and 20 more cycles were performed at 96° C., 30 sec; 67° C., 30 sec; 72° C., 1 min. Upstream primer sequence is

5' CTG GAG AGA CCT GTG ATC CTG AAC C 3' (SEQ ID NO:7)

Secondary product of 621 base pairs was isolated from agarose gel as above, then digested with KpnI and XbaI to generate 474 base pair mutated MSP fragment corresponding to nucleotides 1804 through 2290.

Mutated fragment was subcloned into pCDNA3/mMSP for transient expression in 293/E1 cells and into pDSRα2/mMSP for stable expression in CHO D- cells. Both constructs were sequenced to verify the presence of Cys to Ala mutation. Nucleotide positions refer to those of murine MSP RNA sequence, Genbank accession number M74181.

Transient expression of murine MSP C677A mutant in 293/E1 cells

293/E1 cells were seeded at a density of 1×10[6] cells per 10 cm dish in complete medium (DMEM, high glucose, supplemented with 10% FBS and 0.3 mg/ml L-glutamine) and allowed to incubate overnight at 37°, 5% $CO_2$. Shortly before transfecting, complete medium was removed and replaced with DMEM+5% FBS+0.3 mg/ml L-glutamine, 4 ml per dish.

Plasmid DNAs pCDNA3/mMSP C677A and pCDNA3/mMSP wild type were diluted to 10 ug per 500 ul serum-free DMEM and filter sterilized. A mock sample containing no DNA was also prepared in parallel. Lipofectamine reagent (Life Sciences, Inc., Gaithersburg, Md.) was diluted to 0.2 mg/ml in serum-free DMEM and combined with filter-sterilized plasmid DNA; final concentration for each sample was 10 ug/ml DNA and 0.1 mg/ml lipofectamine in 1 ml each. DNA/lipofectamine mixtures were incubated at room temperature, 30 minutes, then added to cell monolayers. Treated cells were returned to 37° C. for approximately 6 hours, then medium was removed and replaced with fresh DMEM+5% FBS+0.3 mg/ml L-glutamine and cells were allowed to recover overnight.

Transfected cells were then washed once with serum-free DMEM and conditioned for 48 hours in serum-free DMEM+0.3 mg/ml L-glutamine at 9 ml per dish. Conditioned media were harvested, filtered to remove cell debris, and concentrated to 5× in Centriprep-10 concentration units (Amicon, Inc., Beverly, Mass.). Expression of MSP was verified for C677A and wild type samples by Western blot; no expression was seen in mock sample. All three conditioned media samples were assayed for biological activity in murine crypt attachment assay.

Stable expression of C677A in CHO D- cells

CHO D- cells were seeded at $8 \times 10^5$ cells per 60 mm dish in complete medium (DMEM, high glucose, with 10% FBS, 1× PSG, 1× NEAA and 1× HT supplement) in 5 ml per dish and allowed to attach overnight at 37° C. in 5% $CO_2$. Medium was replaced with 5 ml fresh complete medium approximately 3 hours prior to transfection.

Plasmid DNA pDSRa2/mMSP C677A was diluted to 60 ng/ul in 0.25M $CaCl_2$ and filter sterilized. A mock sample containing no DNA was also prepared in parallel. Following sterilization, 250 ul of each sample was combined with 250 ul of 2× HEPES-buffered saline and incubated at room temperature for 30 minutes to allow $CaPO_4$ precipitates to form. Medium was aspirated and $CaPO_4$/DNA samples were added to cells; following a 30 minute incubation at room temperature, cells were fed with 5 ml complete medium per plate and allowed to recover overnight at 37° C. Cells were re-fed with fresh complete medium the next day.

At approximately 72 hours post-transfection, cells were split into selective medium (DMEM with 5% dialyzed FBS, 1× PSG, and 1× NEAA) at a ratio of 1:20 in 10 cm dishes. Viable colonies appeared after about 10 days, and were isolated by ring cloning and expanded for analysis. Mock-transfected cells produced no viable colonies.

Conditioned medium was generated from individual colonies plated into 24-well dishes; serum-free DMEM containing 1× NEAA and 1× PSG was incubated on 80% confluent monolayers at 400 ul per well for 72 hours, then harvested and filtered to remove cellular debris. Following concentration in Microcon-10 concentration units, the equivalent of 30 ul of 1× conditioned medium per well was run on an 8% SDS-PAGE reducing gel. Proteins were electrophoretically transferred to nitrocellulose membrane and blotted with a rabbit polyclonal antibody raised against MSP. Blot was then exposed to horseradish peroxidase-conjugated anti-rabbit secondary antibody and visualized using Enhanced Chemiluminescence (ECL) system (Amersham, Inc.). The highest expression of MSP was seen for clone 2, which was selected for further expansion.

To generate large scale amounts of mMSP C677A mutant protein, CHO/C677A clone 2 cells were seeded into 100 roller bottles in 50% DMEM/50% Ham's F-12 medium supplemented with 5% FBS, 1× NEAA and 1× PSG. When monolayers reached 80% confluency, cells were washed with PBS to remove residual serum and conditioned in serum-free 50% DMEM/50% F-12 with 1× NEAA and 1× PSG for 4 days. A total of 20 liters of conditioned medium was harvested for purification.

EXAMPLE 5

Construction and Expression of Human MSP Mutant

Construction of C672A Mutant of Human MSP

To mutate the Cys residue suspected of interfering with interchain disulfide bond formation, a two-step PCR process was employed. First, human MSP plasmid template was amplified with a mutant primer (which incorporated a change from TG to GC at nucleotides 2024 and 2025, resulting in a Cys to Ala mutation) and a downstream primer complementary to vector pCDNA3 (Invitrogen, San Diego, Calif.). Primer sequences are:

Mutant: 5' CAC AAC GCC TGG GTC CTG GAA G 3' (SEQ ID NO:8)

Downstream: 5' CTG GCA ACT AGA AGG CAC AGT CG 3' (SEQ ID NO:9)

Cycling conditions were: 96° C., 30 sec.; 62° C., 30 sec.; 72° C., 1'for 5 cycles, followed by an additional 15 cycles at 96° C., 30 sec; 67° C., 30 sec; 72° C., 1 min. The primary 323 base pair product was isolated from an agarose gel and purified to remove agarose.

The primary PCR product containing the Cys to Ala mutation was combined with a small amount of the original MSP plasmid template and cycled in the absence of oligonucleotide primers for 5 cycles. This allowed the upstream and downstream extension of the mutated PCR product. Primers corresponding to an upstream region (nucleotides 1576–1598) of huMSP and the downstream vector primer (above) were added, and 20 more cycles were performed at 96° C., 30 sec; 67° C., 30 sec; 72° C., 1 min. Upstream primer sequence is

5' GTG CTT CTC CTC CTG CCA TAT GC 3' (SEQ ID NO:10)

Secondary product of 765 base pairs was isolated from agarose gel as above, then digested with Bgl II and Xba I to generate a 528 base pair mutated MSP fragment corresponding to nucleotides 1736 through 2219, plus a portion of the pCDNA3 multiple cloning site.

The mutated fragment was subcloned into pCDNA3/huMSP for transient expression in 293/E1 cells and into pDSRα2/huMSP for stable expression in CHO D- cells. Both constructs were sequenced to verify the presence of Cys to Ala mutation. Nucleotide positions refer to those of published human MSP cDNA sequence having GenBank accession number L11924 (Yoshimura et al, J. Biol. Chem 268 15461–15468 (1993)).

Transient expression of Human MSP C672A mutant in 293/E1 cells

293/E1 cells were seeded at a density of $1 \times 10^6$ cells per 10 cm dish in complete medium (DMEM, high glucose, supplemented with 10% FBS and 0.3 mg/ml L-glutamine) and allowed to incubate overnight at 37°, 5% $CO_2$. Shortly before transfecting, complete medium was removed and replaced with DMEM+5% FBS+0.3 mg/ml L-glutamine, 4 ml per dish.

Plasmid DNAs pCDNA3/huMSP C672A and pCDNA3/huMSP wild type were diluted to 10 ug per 500 ul serum-free DMEM and filter sterilized. A mock sample containing no DNA was also prepared in parallel. Lipofectamine reagent (Life Sciences, Inc., Gaithersburg, Md.) was diluted to 0.2 mg/ml in serum-free DMEM and combined with filter-sterilized plasmid DNA; final concentration for each sample was 10 ug/ml DNA and 0.1 mg/ml lipofectamine in 1 ml each. DNA/lipofectamine mixtures were incubated at room temperature, 30 minutes, then added to cell monolayers. Treated cells were returned to 37° C. for approximately 6 hours, then medium was removed and replaced with fresh DMEM+5% FBS+0.3 mg/ml L-glutamine and cells were allowed to recover overnight.

Transfected cells were then washed once with serum-free DMEM and conditioned for 48 hours in serum-free DMEM+0.3 mg/ml L-glutamine at 9 ml per dish. Conditioned media were harvested, filtered to remove cell debris, and concentrated to 5× in Centriprep-10 concentration units (Amicon, Inc., Beverly, Mass.). Expression of MSP was verified for C672A and wild type samples by Western blot; no expression was seen in mock sample. All three conditioned media samples were assayed for biological activity in murine crypt attachment assay.

Stable expression of C672A in CHO D- cells

CHO D- cells were seeded at $8 \times 10^5$ cells per 60 mm dish in complete medium (DMEM, high glucose, with 10% FBS, 1× PSG, 1× NEAA and 1× HT supplement) in 5 ml per dish and allowed to attach overnight at 37° C. in 5% $CO_2$. Medium was replaced with 5 ml fresh complete medium approximately 3 hours prior to transfection.

Plasmid DNA pDSRα2/huMSP C672A was diluted to 60 ng/ul in 0.25M $CaCl_2$ and filter sterilized. A mock sample containing no DNA was also prepared in parallel. Following sterilization, 250 ul of each sample was combined with 250 ul of 2× HEPES-buffered saline and incubated at room temperature for 30 minutes to allow $CaPO_4$ precipitates to form. Medium was aspirated and $CaPO_4$/DNA samples were added to cells; following a 30 minute incubation at room temperature, cells were fed with 5 ml complete medium per plate and allowed to recover overnight at 37° C. Cells were re-fed with fresh complete medium the next day.

At approximately 72 hours post-transfection, cells were split into selective medium (DMEM with 5% dialyzed FBS, 1× PSG, and 1× NEAA) at a ratio of 1:20 in 10 cm dishes. Viable colonies appeared after about 10 days, and were isolated by ring cloning and expanded for analysis. Mock-transfected cells produced no viable colonies.

Conditioned medium was generated from individual colonies plated into 24-well dishes; serum-free DMEM containing 1× NEAA and 1× PSG was incubated on 80% confluent monolayers at 400 ul per well for 48 hours, then harvested and filtered to remove cellular debris. Following concentration in Microcon-10 concentration units, the equivalent of 30 ul of1× conditioned medium per well was run on an 8% SDS-PAGE reducing gel. Proteins were electrophoretically transferred to nitrocellulose membrane and blotted with a mouse monoclonal antibody raised against MSP. Blot was then exposed to horseradish peroxidase-conjugated anti-mouse secondary antibody and visualized using Enhanced Chemiluminescence (ECL) system (Amersham, Inc.). The highest expression of MSP was seen for clone 3, which was selected for further expansion.

EXAMPLE 6

Purification of Recombinant MSP

Conditioned media, with or without concentration by diafiltration, and without salt or pH adjustment, was chromatographed by absorption onto heparin-Sepharose (Pharmacia), and elution with a salt gradient in 20 mM sodium phosphate, pH 7. MSP eluted at 0.4M NaCl. Pooled fractions were dialyzed with 0.02 M Tris, pH 8.5 and chromatographed by absorption on Q Sepharose HP (Pharmacia), and elution with a salt gradient in 0.02 M Tris pH 8.5. MSP eluted at 0.1 M salt.

MSP was activated by either by incubation at 37° C. for one hour with 10 μg/ml human kallikrein (Enzyme System Products), followed by addition of 1 mM pefabloc (Boeringher Mannheim) or by passing through a column of kallikrein-Sepharose (1 mg/ml human kallikrein/ml cyanogen bromide activated Sepharose, 4 ml total). Active samples were dialyzed versus phosphate buffered saline.

MSP was analyzed with 10% PAGE gels from Novex. Non reduced samples were mixed with sample buffer containing SDS but were not heated. Reduced samples were heated at 90° C. for three minutes in sample buffer which contained SDS and 5% β-mercaptoethanol. The results are shown in FIG. 4. Purified recombinant murine and human MSP and murine C677A and human C672 analogs appear as a proform consisting of a single band of about 80 kDa when analyzed by SDS-PAGE under reducing (lanes 1 or 3) or nonreducing conditions (lanes 5 or 7), with Coomassie blue staining. Kallikrein treatment efficiently cleaves proMSP or proMSP analog between the α and β subunits, as shown by SDS-PAGE under reducing conditions (lanes 2 and 6). However, the subunits of kallikrein-treated, recombinant, nonmutant MSP do not remain linked during SDS-PAGE under nonreducing conditions (lane 4). The kallikrein-treated analog of MSP described does remain linked during SDS-PAGE under nonreducing conditions, apparently due to the sparing of the intersubunit disulfide bond (lane 8).

EXAMPLE 7

Activity of Recombinant MSP and MSP Analogs

Figure 5:
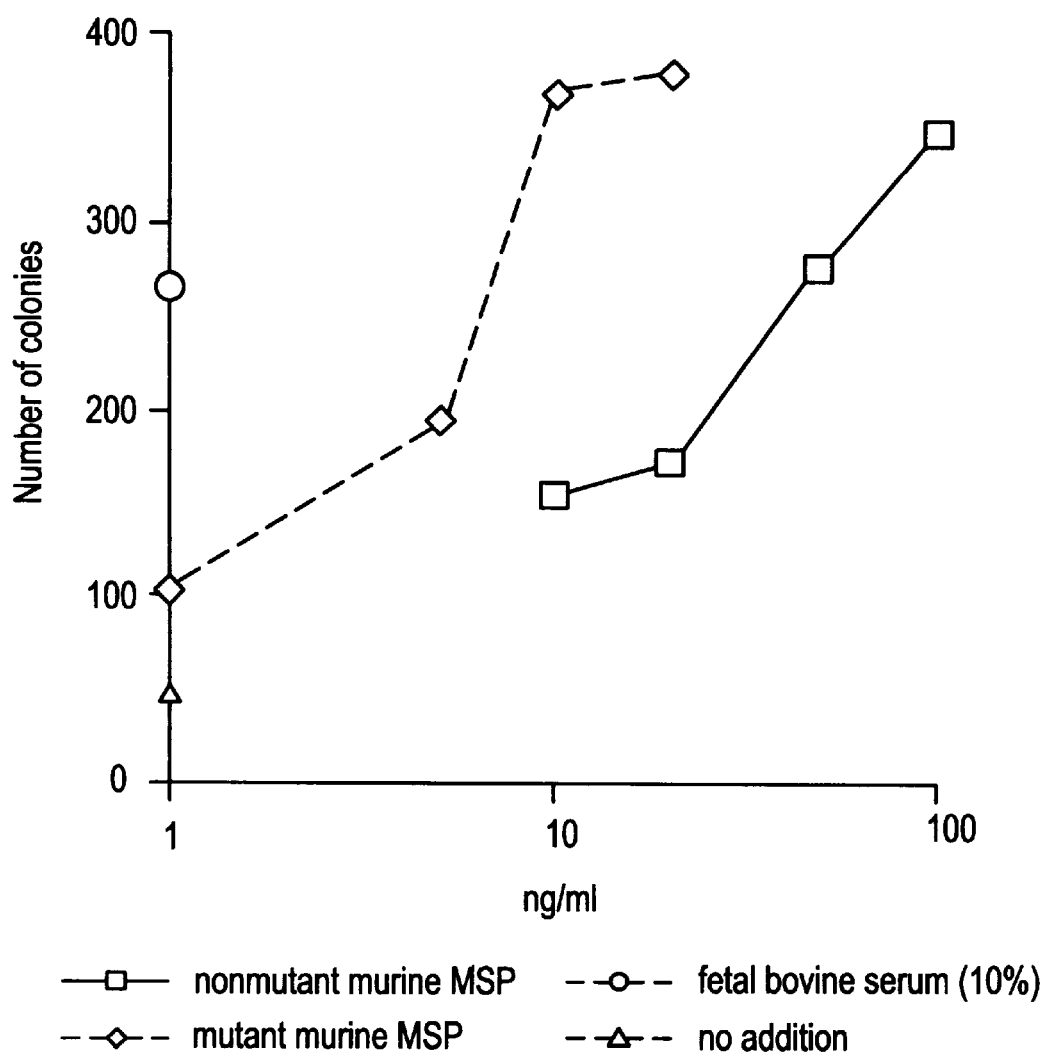
FIG. 5 shows activity of purified murine and C677A MSP in crypt attachment assay. Purified mMSP mutant C677A protein was assayed in parallel with wild-type mMSP for biological activity in murine crypt attachment assay. Samples were treated with Kallikrein at 15 µg/ml for 30 minutes at 37° C., then added to mouse colonic crypts at the final concentrations as shown. Treated crypts were plated in the wells of collagen-coated tissue culture plates, and were allowed to incubate overnight, followed by staining and counting of attached crypts. Values are plotted as fold stimulation over untreated wells. Purified bovine MSP was used as a positive control in this assay Kallikrein-cleaved mutant MSP gives approximately 10-fold higher specific activity than cleaved wild type MSP in this assay.
Figure 6:
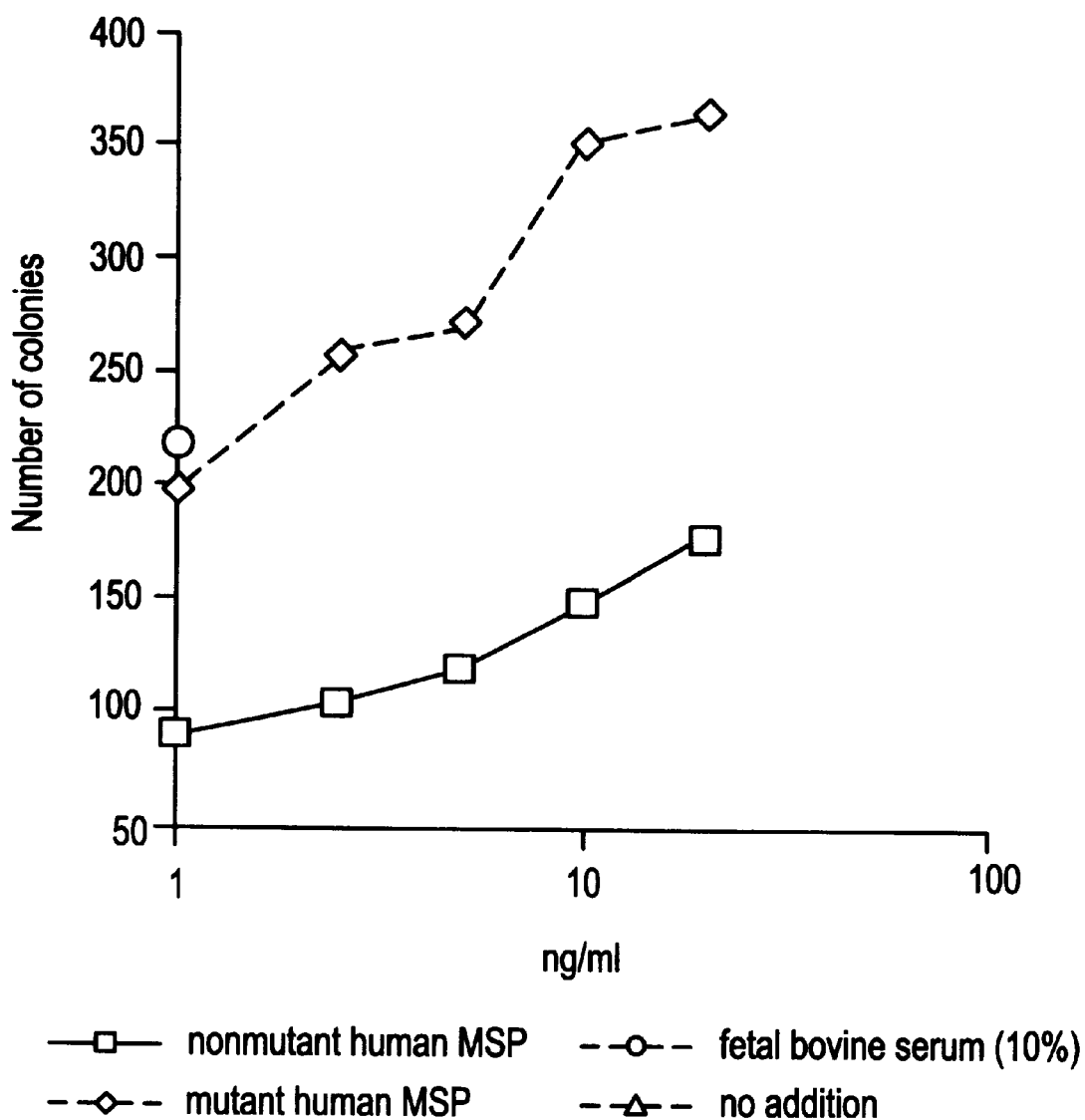
FIG. 6 shows activity of purified human MSP and C672A MSP mutant in crypt attachment assay.

Recombinant murine MSP and C677A analog expressed and purified as described in Example 4 and recombinant human MSP and C672A analog expressed and purified as described in Example 5 were assayed for colony forming activity as described in Example 1. The results for murine MSP are shown in FIG. 5 and the results for human MSP are shown in FIG. 6.

Figure 7:
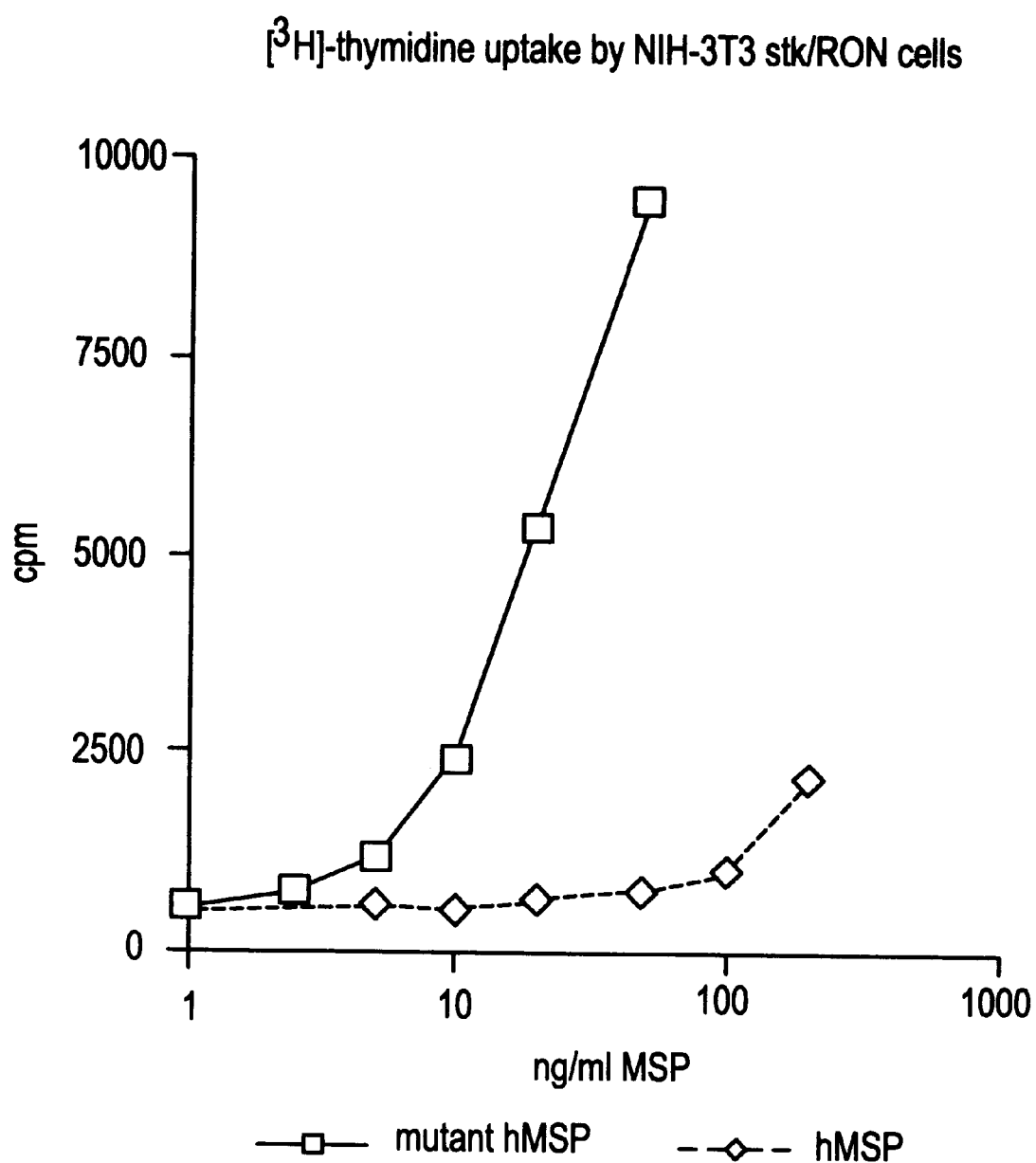
FIG. 7 shows $^3$H thymidine uptake by NIH 3T3 cells expressing RON at the cell surface by purified human MSP and C672A MSP mutant.

Recombinant human MSP and the C672A analog were assayed for stimulation of $^3H$ thymidine uptake by cells expressing the stk/RON receptor. The full length cDNA for murine stk/RON (GenBank accession number x74736) was cloned using standard techniques, subcloned into the mammalian expression vector, pEV7, and tritiated thymidine uptake was measured in NIH 3T3 cells expressing stk/RON as described (Zhang et al. J. Biol. Chem. 271, 3884–3890 (1996)). The results are shown in FIG. 7.

While the invention has been described in what it considered to be its preferred embodiments, it is not limited to the disclosed embodiments, but on the contrary, is intended to cover various modifications and equivalents included within the spirit and scope of the appended claims, which scope is to be accorded the broadest interpretation so as to encompass all such modifications and equivalents.

What is claimed is:

1. A purified and isolated analog of mature macrophage stimulating protein (MSP) wherein at least one unpaired cysteine residue has been substituted with another amino acid.

2. The analog of claim 1 which is derived from mammalian MSP.

3. The analog of claim 2 which is derived from human MSP.

4. The analog of claim 1 wherein a cysteine residue at position 677 of SEQ ID NO:1 or a cysteine residue at position 672 of SEQ ID NO:2 has been substituted with another amino acid.

5. The analog of claim 1 which is substantially free of other human proteins.

6. The analog of claim 1 which is characterized by being a product of expression of an exogenous DNA sequence.

7. The analog of claim 6 wherein the exogenous DNA sequence is cDNA, genomic DNA or synthetic DNA.

8. The analog of claim 1 which has been modified with a water-soluble polymer.

9. The analog of claim 8 wherein the water soluble polymer is polyethylene glycol.

10. A pharmaceutical composition comprising the MSP analog of claim 1 in a pharmaceutically acceptable carrier, adjuvant, solubilizer, stabilizer and/or anti-oxidant.

11. The composition of claim 10 wherein the analog is derived from human MSP.

12. The composition of claim 10 wherein the MSP analog has a cysteine residue at position 672 of SEQ ID NO:2 substituted with another amino acid.

* * * * *

UNITED STATES PATENT AND TRADEMARK OFFICE
CERTIFICATE OF CORRECTION

PATENT NO. : 5,948,892
DATED : September 7, 1999
INVENTOR(S) : Robert C. Wahl

It is certified that error appears in the above-identified patent and that said Letters Patent is hereby corrected as shown below:

Column 10, line 7, change "a" to -- $\alpha$ --.

Signed and Sealed this

Twenty-ninth Day of August, 2000

Attest:

Q. TODD DICKINSON

Attesting Officer

Director of Patents and Trademarks